United States Patent [19]

Slavin

[11] Patent Number: 4,489,610

[45] Date of Patent: Dec. 25, 1984

[54] COMPUTERIZED AUDIOMETER

[75] Inventor: Martin J. Slavin, Dix Hills, N.Y.

[73] Assignee: Intech Systems Corp., Hauppauge, N.Y.

[21] Appl. No.: 599,152

[22] Filed: Apr. 11, 1984

[51] Int. Cl.³ .............................................. H04R 29/00
[52] U.S. Cl. ........................................ 73/585; 128/746
[58] Field of Search ................. 73/585, 645, 646, 647, 73/648; 364/415; 128/746; 179/107 FD, 107 R

[56] References Cited

U.S. PATENT DOCUMENTS

| | | | |
|---|---|---|---|
| 3,808,354 | 4/1974 | Feezor et al. | 73/585 |
| 3,809,811 | 5/1974 | Delisle et al. | 73/585 |
| 3,989,904 | 11/1976 | Rohrer et al. | 179/107 FD |
| 3,996,928 | 12/1976 | Marx | 364/415 |
| 4,024,499 | 5/1977 | Bosscher | 73/585 |
| 4,107,465 | 8/1978 | Charlebois et al. | 73/585 |
| 4,122,518 | 10/1978 | Castleman et al. | 364/415 |
| 4,157,456 | 6/1979 | Voss | 73/585 |
| 4,216,462 | 8/1980 | McGrath et al. | 364/415 |
| 4,284,847 | 8/1981 | Besserman | 73/585 |

Primary Examiner—Stephen A. Kreitman
Attorney, Agent, or Firm—Blum, Kaplan, Friedman, Silberman & Beran

[57] ABSTRACT

A computerized audiometer is provided with at least one head set, a control switch, a tone generator for providing a plurality of sequential tones of different frequencies and amplifications to at least one head set, and a central processing unit for receiving data representative of the response to the test of the person being tested as reflected by the operation of the control switch. The central processing unit is adapted to analyze the test data and produce a program representative of the correction required by the person being tested. The audiometer is provided with a programming output adapted for coupling to a hearing aid for programming a hearing aid by applying the program developed by the central processing unit to the hearing aid.

15 Claims, 2 Drawing Figures

COMPUTERIZED AUDIOMETER

BACKGROUND OF THE INVENTION

This invention relates generally to a computerized audiometer used in testing hearing. Specifically, it is directed to a computerized audiometer for testing the hearing of one person or variable numbers of people at the same time, and for generating programming for a programmable hearing aid. While the art of audiometers is generally well known and well understood, the conversion of audiometric screening information into a form incorporatable in a hearing aid specifically programmed to remedy the specific hearing deficiencies of the user has proved difficult. It is well known in the medical arts relating to the human hearing function, that most hearing loss does not take place equally across the entire audio frequency spectrum, but rather is localized to certain frequency ranges, with variable hearing losses at varying frequency ranges. While audiometers have been developed that will automatically conduct hearing test screenings through a range of frequencies and amplitudes, it has not been heretofore possible to analyze and convert the data obtained through the audiometric screening into data for programming a hearing aid capable of variably adjusting the amplification of sound in frequency bands characterized by variable widths and/or center frequencies.

Further, it is desirable to provide a computerized audiometer which can efficiently and automatically perform hearing tests on one or a variable number of people, store or transmit information on the people being tested including identification and test data and actually program a hearing aid to the desired correction.

SUMMARY OF THE INVENTION

Generally speaking, in accordance with the present invention, an improved computerized audiometer for testing the hearing of one or more of a variable number of people at the same time and generating programming for a programmable hearing aid is provided. The audiometer includes at least one head set and control switch for use by the person being tested, a tone generator for applying a selected sequence of tones of varying frequency and amplification to the head set under the control of a central processing unit, a memory for storing the results of the test for analysis by the central processing unit, and output means adapted to program a hearing aid in accordance with the results of said analysis when coupled thereto. An audible instruction generator may be coupled to the head set for providing an automatic sequence of spoken instructions to the person being tested. The output of the tone generator may be fed back for comparison with the desired frequency to assure accuracy of output. The tone generator may be adjustable to reflect the results of such feedback. The audiometer may be under the control of an operator provided with a display and keyboard coupled to the central processing unit. Local and remote printers, data storage and modum devices may be provided.

Accordingly, it is an object of the invention to provide an improved computerized audiometer.

Another object of the inventon is to provide an improved computerized audiometer capable of directly programming a programmable hearing aid.

A further object of the invention is to provide an improved computerized audiometer capable of automatic computer-controlled testing including regulation of the output frequencies.

Still other objects and advantages of the inventon will in part be obvious and will in part be apparent from the specification.

The invention accordingly comprises the features of construction, combinations of elements, and arrangements of parts which will be exemplified in the construction hereinafter set forth and the scope of the invention will be indicated in the claims.

BRIEF DESCRIPTION OF THE DRAWINGS

For a fuller understanding of the inventon, references had to the following description taken in connection with the accompanying drawings, in which.

DETAILED DESCRIPTION OF THE PREFERRED EMBODIMENT

Figure 1:
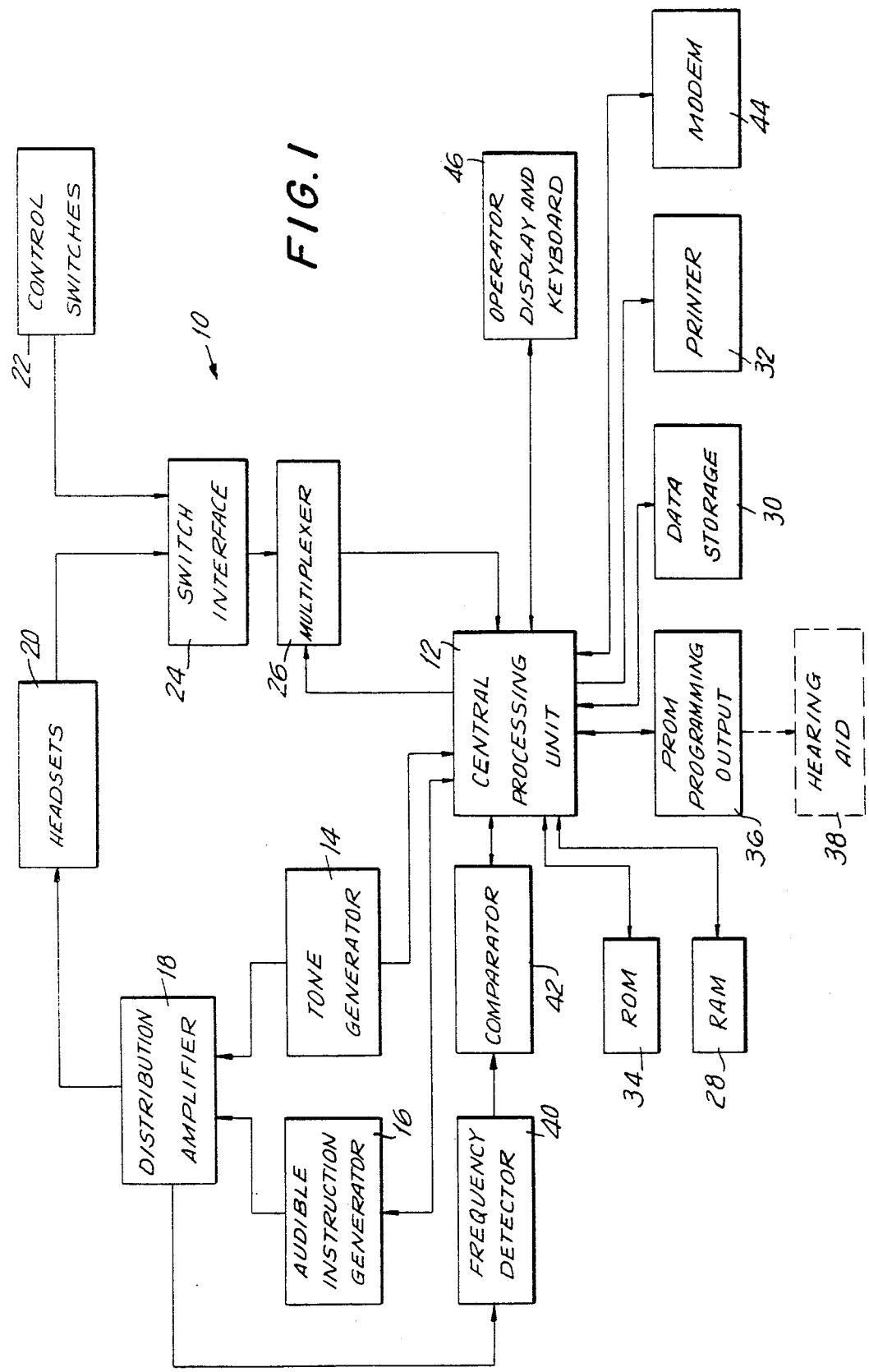
FIG. 1 is a block diagram illustrating the computerized audiometer in accordance with the invention.

Reference is now made to the block diagram of FIG. 1 showing the computerized audiometer 10 in accordance with the invention. The audiometer includes a central processing unit 12 which controls the operation thereof. Among the outputs controlled by the central processing unit 12 is tone generator 14 adapted to produce, under the control of central processing unit 12, a sequence of tones of varying frequency and amplification which constitutes the test. Pauses would be built into the sequence to permit audible instruction as by means of audible instruction generator 16. Audible instruction generator 16 may take the form of a continuously cyclable tape or record player or a voice synthesizer operating under the control of the central processing unit and adapted to provide a series of audible instructions to the user for the conduct of the test in the proper sequence and with the proper pauses, the instructions being coordinated with the outputs of the tone generator 14. The outputs of audible instruction generator 16 and tone generator 14 are applied to a distribution amplifier 18 which in turn applies the outputs to one or a plurality of head sets 20. This arrangement permits the simultaneous conduct of a plurality of tests, provided each person to be tested is provided with a head set 20 and a control switch 22. The control switches 22 permit the person being tested to indicate when an audible signal is heard or not heard, as desired. The control switches are coupled through switch interface 24 and multiplexer 26 to the central processing unit 12. The multiplexer, which operates in response to timing signals from the central processing unit, sequentially polls the various switches so that the central processing unit can identify, by the time position, the person to whom the response is attributable. A switch is provided in the receptacle in which each of head sets 20 is plugged so that the switch interface can detect when a head set is in use. In this way, the response to the sequence of tones produced by tone generator 14 is fed back to the central processing unit 12 which stores that data for processing in a random access memory (RAM) 28. The data may be simultaneously stored in other data storage means 30 such as a tape, a disc or a bubble memory and may be printed out as by printer 32. On the other hand, the data can be stored through the completion of the test in RAM 28 and later fed to the data storage device 30 or printer 32 after processing together with identifying data supplied as more particularly described below.

The program for the operation of central processing unit 12 is contained in a read-only memory (ROM) 34. Included within the program of ROM 34 is a program for analyzing the data derived from the conduct of each test and determining the correction required in terms of frequency band and amplification within that band. Specifically, in an application of Martin J. Slavin entitled Differential Hearing Aid With Programmable Frequency Response, assigned to the assignee of the instant application, a programmable hearing aid is taught having a plurality of programmable switched capacitor filter circuits capable of providing a controlled frequency response based on a pre-programmed digital information which is stored within the hearing aid in an electrically programmable read-only memory (EPROM). By adjusting the stored information, the center frequency of each frequency band can be selected, the band width itself can be selected and the degree of amplification for that band can be selected. Using the program stored in ROM 34, the central processing unit 12 calculates from the test data the desired correction in the form of digital instructions which may be temporarily stored in RAM 28, printed out by printer 32 or more permanently stored in data storage 30. More important, these digital instructions (a program) can be applied to PROM programming output 36 adapted to mate with and coupled to a programmable hearing aid 38 to "burn" the desired program into the EPROM of the hearing aid so that the hearing aid is now tailored specifically to the needs of the person being tested.

In one embodiment of the hearing aid, National Semiconductor MF 10 Universal Monolithic Dual Switched Capacitor Filter chips may be used in conjunction with external resistors an external clock and an operational amplifier. The value of the resistors, the frequency of the clock and the amplification of the operational amplifier may be digitally set as by controlling MOS gates through a control circuit in response to the program stored in the EPROM of the hearing aid. In this manner, the center frequency and band width of a plurality of frequency bands requiring correction can be selected and each band selectively amplified to provide the desired correction.

In order to operate the audiometer, an operator display and keyboard 46 is provided coupled to the CPU. This device permits the operator to input the CPU for storage and/or printout, identifying informaton concerning the person being tested, the nature of the test being conducted, the situs of the test, insurance information, and the like. The operator keyboard and display also permits the operator to selectively tailor the conduct of the test as desired. A display is provided so that the operator can insure the correctness of inputs before providing them to the central processing unit. Also, if desired, the test results and even the program can be displayed to the operator so that he can monitor the operation of the audiometer and the programming of the hearing aid.

Since the audiometer 10 in accordance with the invention is intended for automatic operation and programming of a hearing aid, it is important that the tone generator 14 operate accurately. In order to preserve such accuracy, the output of distribution amplifier 18 is fed back to frequency detector 40 which determines the frequency of the output tone and a value representative of that frequency is applied to a comparator 42. The central processing unit applies a value to the comparator representative of the frequency which should be applied by the tone generator at that point in time and the comparator provides an indication of the accuracy of the tone generator. Defects in the tone generator output can cause aborting of the test to permit manual correction or can cause, pursuant to a program in the central processing unit, the automatic adjusting of the tone generator and modification of the test to cure the defect, or both.

While the arrangement depicted is adapted for local testing, storage and control, the central processing unit can be coupled by a modem 44 to a remote testing site or to remote data storage and printing devices.

Figure 2:
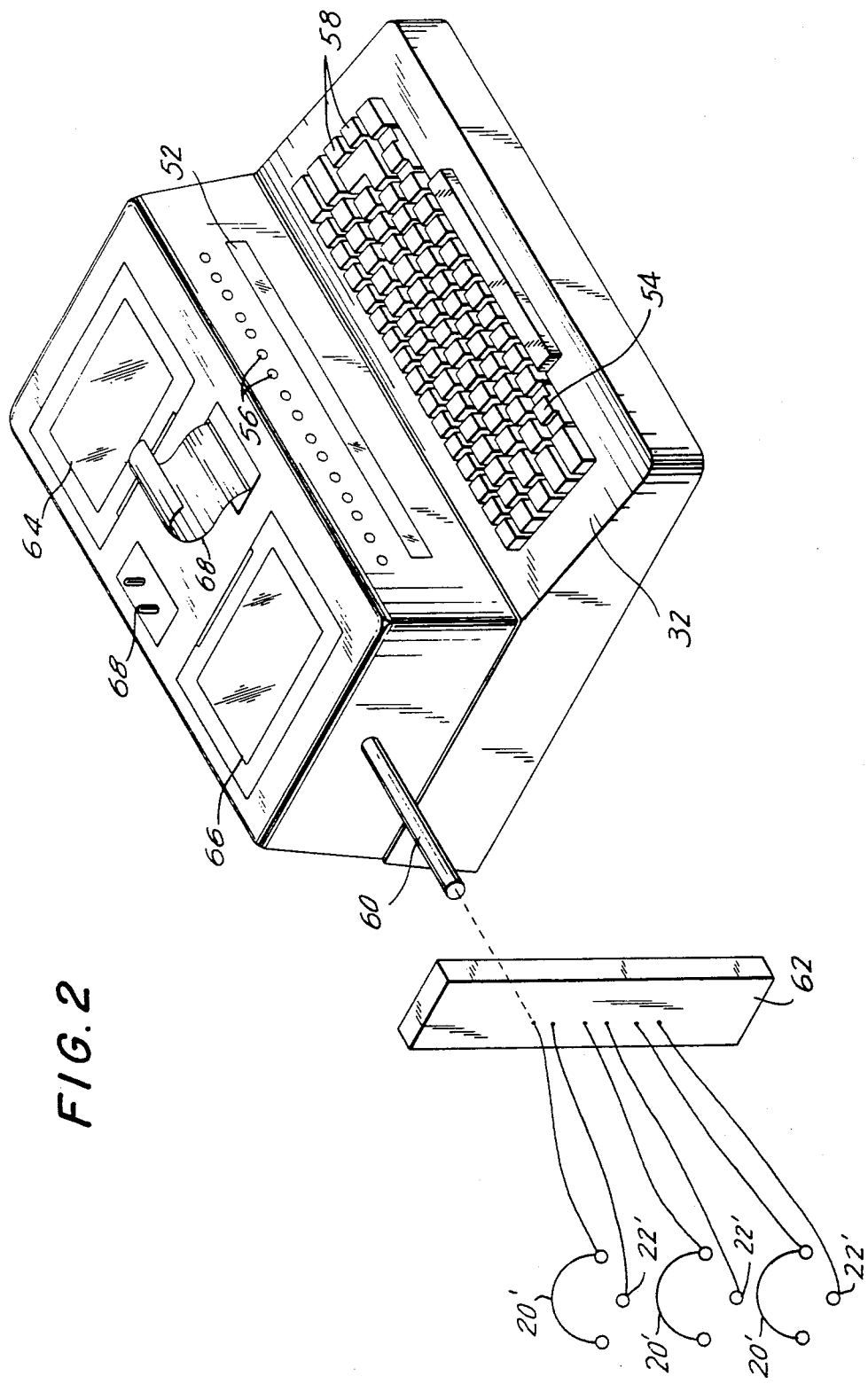
FIG. 2 is a perspective view of one embodiment of a computerized audiometer showing a hearing aid coupled thereto for programming.

Referring to FIG. 2, a cabinet 50 is depicted having a display 52, a keyboard 54, status lamp indicators 56 and dedicated control switches 58. Generally, cabinet 50 houses the central processing unit, tone generator, distribution amplifier, feedback arrangement, memories and the like. Audible instructions are provided by magnetic cassette reader 64, data storage is provided in the form of a magnetic cassette recorder 66 and a printer 68 is provided. The cabinet is connected by a cable 60 to a switch and head set distribution box 62 to which a plurality of head sets 20' are releasably coupled, one switch 22' being associated with each head set 20'. Housing 50 is also provided with a hearing aid coupling output 68 adapted to receive and couple to a hearing aid to permit "burning" of the EPROM thereof, or adapted to receive a plugable EPROM itself for the same purpose.

While the embodiment of the computerized audiometer depicted is particularly adapted for a plurality of simultaneous tests, the device could equally be adapted to conduct a single test at a time. Further, while the device described is particularly adapted to create a particular type of program for programming a hearing aid which utilizes switched capacitor filter circuits, the arrangement is equally applicable to other programming schemes.

It will thus be seen that the object set forth above, and those made apparent from the preceding description, are effectively attained and, since certain changes may be made in the above constructions without departing from the spirit and scope of the invention, it is intended that all matter contained in the above description shown in the accompanying drawings shall be interpreted as illustrative and not in a limiting sense.

It is also to be understood that the following claims are intended to cover all the generic and specific features of the invention herein described and statements of the scope of the invention which, as a matter of language, might be said to fall therebetween.

What is claimed is:

1. A computerized audiometer comprising at least one head set;
   a control switch actuable by the person being tested and associated with each head set;
   tone generator means for applying a predetermined sequence of tones of varying frequency and amplification to said at least one head set for conducting an audiometric test; and
   a central processing unit coupled to said control switch for detecting the actuation thereof in coordination with the operation of the tone generator means, said central processing unit being adapted to process the outputs of said control switch and determine a program representative of the corrections required by the person being tested in terms of frequency band and amplification within each frequency band in a form suitable for programming a programmable hearing aid to conform to the correction required by the person being tested.

2. The computerized audiometer as recited in claim 1, including a plurality of head sets and a control switch associated with each of said head sets, and including multiplexer means for sequentially polling each of said control switches.

3. A computerized audiometer as recited in claim 1, including means coupled to the output of said tone generator means for detecting the frequency of said output and for comparing said frequency output to the desired frequency output to provide an indication of the accuracy of the frequency of the output tone generator.

4. A computerized audiometer as claimed in claim 1, wherein said program is adapted to program the center frequency of a plurality of switched capacitor filter circuits and the amplification of the outputs of each of said circuits.

5. A computerized audiometer as recited in claim 1, including audible instruction generator means coupled to said head sets for providing audible instructions for the conduct of the test to the person being tested.

6. A computerized audiometer as recited in claim 5, wherein said central processing unit is coupled to said tone generator means and audible instruction generator means for the control thereof.

7. A computerized audiometer as recited in claim 1, including a read-only memory (ROM) for storing the program for the operaton of said computerized audiometer and memory means for storing the results of said test.

8. A computerized audiometer as recited in claim 1, including input keyboard means coupled to the central processing unit for the input of data.

9. A computerized audiometer as recited in claim 8 including display means for displaying the output of said keyboard.

10. A computerized audiometer as recited in claim 1, including memory means for storing said program representative of said corrections.

11. A computerized audiometer as recited in claim 1, including an output means coupleable to a programmable hearing aid for applying said program thereto.

12. A computerized audiometer as recited in claim 1 coupleable to an EPROM of a programmable hearing aid for applying said program thereto.

13. A computerized audiometer as recited in claim 1, wherein said program is adapted to determine the center frequency and band amplification of at least one frequency band required for correction.

14. A computerized audiometer recited in claim 13, wherein said program is adapted to determine the band width of said at least one frequency band.

15. A computerized audiometer as recited in claim 13, wherein said program is adapted to determine the center frequency and amplification of a plurality of frequency bands required for correction.

* * * * *